United States Patent [19]

Mobilio

[11] Patent Number: 4,783,479
[45] Date of Patent: Nov. 8, 1988

[54] SUBSTITUTED FUSED TETRAHYDROCARBAZOLE ACETIC ACID DERIVATIVES, COMPOSITIONS AND USE

[75] Inventor: Dominick Mobilio, Franklin Park, N.J.

[73] Assignee: American Home Products Corporation, New York, N.Y.

[21] Appl. No.: 184,468

[22] Filed: Apr. 21, 1988

[51] Int. Cl.$^4$ .................... A61K 31/40; C07D 209/80; C07D 209/82
[52] U.S. Cl. ..................................... 514/410; 548/420
[58] Field of Search ........................ 548/420; 514/410

[56] References Cited

U.S. PATENT DOCUMENTS 1,948,923  2/1934  Kalischer et al. .................. 548/420

Primary Examiner—Robert W. Ramsuer
Attorney, Agent, or Firm—Walter Patton

[57] ABSTRACT

Substituted fused tetrahydrocarbazole acetic acid derivatives and methods for their preparation and use are disclosed. The compounds are useful analgesic and anti-inflammatory agents.

8 Claims, No Drawings

SUBSTITUTED FUSED TETRAHYDROCARBAZOLE ACETIC ACID DERIVATIVES, COMPOSITIONS AND USE

This invention relates to novel tetrahydrocarbazole acetic acid derivatives possessing lipoxygenase inhibitory and/or cyclooxygenase inhibitory activity which are useful as anti-inflammatory and antiallergic agents. For instance, they exhibit analgesic and anti-inflammatory activity at dose levels which do not elicit undesirable side effects. The foregoing combination of attributes render the compounds of this invention useful for the treatment of inflammatory conditions and of pain and allergy.

BACKGROUND OF THE INVENTION

It is known that arachidonic acid (AA) is metabolized in mammals by two distinct pathways. The metabolism of arachidonic acid by cycloxygenase enzymes results in the production of prostaglandins and thromboxanes. The physiological activity of the prostaglandins has already been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$, $D_4$ and $E_4$. The substance denominated slow-reacting substance of anaphylaxis (SRS-A) has been shown to consist of a mixture of sulfidopeptide leukotrienes, $C_4$, $D_4$ and $E_4$ [see Back et al, J. Immun., 215, 115–118 (1980); Biochem. Biophys. Res. Commun. 93, 1121–1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al, Nature, 288, 484–486 (1980) and Piper, Int. Arch. Appl. Immunol., 76, suppl. 1, 43 (1985)] which stimulate the release of mucus from airways in vitro [Marom et al, Am. Rev. Resp. Dis., 126, 449 (1982)], are potent vasodilators in skin [see Bisgaard et al, Prostaglandins, 23, 797 (1982)], and produce a wheal and flare response [Camp et al, Br. J. Pharmacol., 80, 497 (1983)]. The nonpeptide leukotriene, $LTB_4$, is a powerful chemotactic factor for leukocytes [see A. W. Ford-Hutchinson, J. Roy. Soc. Med., 74, 831–833 (1981)], which stimulates cell accumulation and affects vascular smooth muscle [see Bray, Br. Med. Bull., 39, 249 (1983)]. The activity of leukotrienes as mediators of inflammation and hypersensitivity is extensively reviewed in Bailey and Casey, Ann. Reports Med. Chem., 17, 203–217 (1982) and in Bray, Agents and Actions, 19, 87 (1986).

Accordingly, the biological activity of the leukotrienes and SRS-A's, and of lipoxygenase as the enzyme leading to the metabolism of AA to leukotrienes, indicates that a rational approach to drug therapy to prevent, remove, or ameliorate the symptoms of allergies, anaphylaxis, asthma and inflammation must focus on blocking the release of mediators of these conditions. Thus, compounds which control the biosynthesis of the leukotrienes and SRS-A's by inhibiting lipoxygenase, are considered to be of value in treating such conditions as allergic bronchial asthma, allergic rhinitis, as well as in other immediate hypersensitivity reactions.

a. Field of Invention

This invention relates to tetracyclic acetic acid derivatives, to their preparation and use, and to intermediates used for their preparation.

More specifically, this invention relates to tetracyclic acetic acid derivatives in which the tetracyclic portion thereof is characterized by having an indole portion fused to a cyclohexane ring and the cyclohexane ring fused to a cycloalkyl ring. Still more specifically, the compounds of this invention are characterized as derivatives of the following tetracyclic acetic acid system:

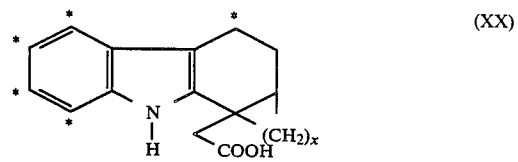

fused tetrahydrocarbazole acetic acid in which the starred carbons are further substituted wherein x is an integer from 1 to 5.

b. Prior Art

The closest prior art to the present invention is:

Mobilio et al, U.S. Pat. No. 4,709,048. Mobilio et al, discloses substituted 2,3,4,9-tetrahydro-1H-carbazole-1-acetic acid derivatives having analgesic and anit-inflammatory activity. The compounds of the present invention differ by the fusion of a cycloalkyl ring to 2,3,4,9-tetrahydro-1H-carbazole-1-acetic acid derivatives.

Demerson et al, U.S. Pat. No. 3,939,178 discloses 1,3,4,9-tetrahydropyrano[3,4-b]indoles and 1,3,4,9-tetrahydrothiopyrano[3,4-b]indoles having analgesic and anti-inflammatory activity. Related U.S. Pat. Nos. are 3,974,179 and 3,843,681.

SUMMARY OF THE INVENTION

The compounds of this invention are represented by formula (I)

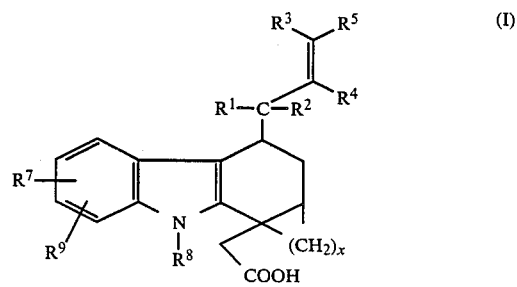

wherein $R^1$, $R^2$, $R^3$, $R^4$ and $R^5$ are independently hydrogen or lower alkyl; or $R^1$ and $R^3$ are joined together to form $(CH_2)_m$; or $R^4$ and $R^5$ are joined together to form —CH=CH—CH=CH—, or $(CH_2)_n$ $R^7$ is hydrogen, lower alkyl, or halogen; $R^8$ is hydrogen or lower alkyl; $R^9$ is hydrogen, lower alkyl, halogen, or acetyl; m is 2 to 3, n is 2 to 4 and x is 1 to 5; and the pharmaceutically acceptable salts thereof.

A preferred aspect of the present invention are the compounds represented by formula (II)

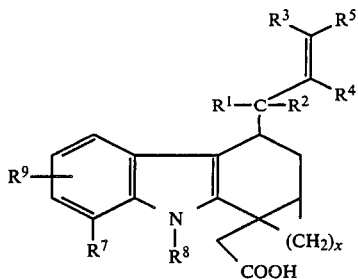

wherein $R^1$, $R^2$, $R^3$, $R^4$ and $R^5$ are independently hydrogen or lower alkyl containing 1 to 6 carbon atoms; or $R^1$ and $R^3$ are joined together to form $(CH_2)_3$; or $R^4$ and $R^5$ are joined together to form —CH=CH—CH=CH—, or $(CH_2)_4$, $R^7$ is hydrogen, lower alkyl containing 1 to 6 carbon atoms, or halogen; $R^8$ is hydrogen or lower alkyl containing 1 to 6 carbon atoms; $R^9$ is hydrogen, lower alkyl containing 1 to 6 carbon atoms, halogen, or acetyl; x is 1 to 5 and the pharmaceutically acceptable salts thereof.

A still further preferred aspect of the present invention are the compounds represented by formula (III)

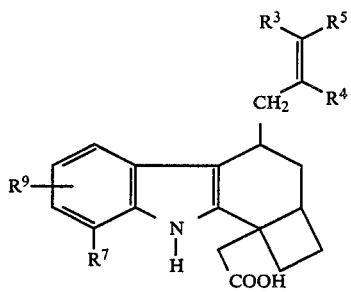

wherein $R^3$, $R^4$ and $R^5$ are hydrogen; or $R^4$ and $R^5$ are joined together to form —CH=CH—CH=CH—; $R^7$ is hydrogen, methyl, ethyl, or propyl; $R^9$ is hydrogen, halogen, or acetyl; and the pharmaceutically acceptable salts thereof.

Another aspect of the present invention are the compounds represented by formula (Ia)

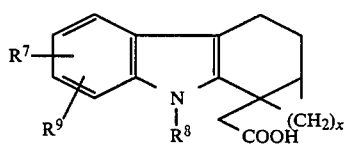

wherein $R^7$ is hydrogen, lower alkyl containing 1 to 6 carbon atoms or halogen; $R^8$ is hydrogen or lower alkyl containing 1 to 6 carbon atoms; and $R^9$ is hydrogen, lower alkyl containing 1 to 6 carbon atoms, halogen, or acetyl; x is 1 to 5 and the pharmaceutically acceptable salts thereof.

Another preferred aspect of the present invention are the compounds represented by formula (IIa)

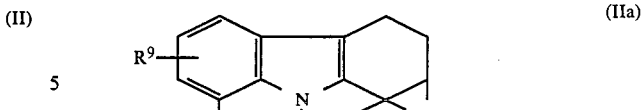

wherein $R^7$ is hydrogen, lower alkyl containing 1 to 6 carbon atoms or halogen; $R^8$ is hydrogen or lower alkyl containing 1 to 6 carbon atoms; and $R^9$ is hydrogen, lower alkyl containing 1 to 6 carbon atoms, halogen, or acetyl; x is 1 to 5 and the pharmaceutically acceptable salts thereof.

A more preferred aspect of the present invention are the compounds represented by formula (IIIa)

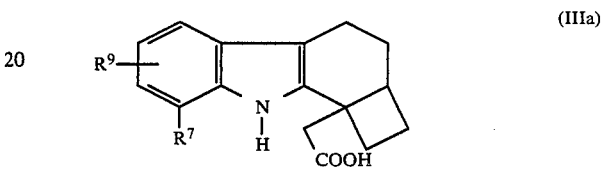

wherein $R^7$ is hydrogen, methyl, ethyl, or propyl; $R^9$ is hydrogen, halogen, or acetyl and the pharmaceutically acceptable salts thereof.

The most preferred compounds of the present invention are designated cis-7-chloro-1,2,2a,3,4,9-hexahydro-8-methyl-4-(phenylmethyl)-9bH-cyclobuta[a]carbazole-9b-acetic acid; cis-7-chloro-1,2,2a,3,4,9-hexahydro-8-methyl-9bH-cyclobuta[a]carbazole-9b-acetic acid; cis-8-ethyl-1,2,2a,3,4,9-hexahydro-9bH-cyclobuta[a]carbazole-9b-acetic acid; cis-1,2,2a,3,4,9-hexa-hydro-9bH-cyclobuta-[a]carbazole-9b-acetic acid; cis-6-acetyl-1,2,2a,3,4,9-hexahydro-8-propyl-9bH-cyclobuta[a]carbazole-9b-acetic acid; and the pharmaceutically acceptable salts thereof.

Some of the compounds of the present invention are prepared by a process in which the unsaturated ketone of structure (IV)

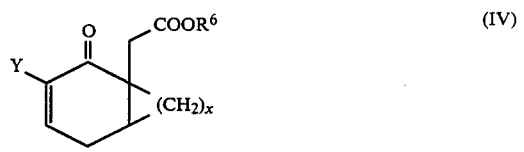

wherein $R^6$ is lower alkyl; Y is bromine or chlorine; and x is 1 to 5 is reacted with the organometallic reagent

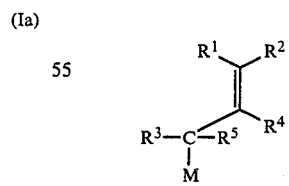

wherein $R^1$, $R^2$, $R^3$, $R^4$ and $R^5$ are hydrogen or lower alkyl; or $R^1$ and $R^3$ are joined together to form $(CH_2)_m$; or $R^4$ and $R^5$ are joined together to form $(CH_2)_n$, wherein m is 2 to 3, and n is 2 to 4; and M is $SiR^{10}R^{11}R^{12}$ or $SnR^{10}R^{11}R^{12}$ wherein $R^{10}$, $R^{11}$ and $R^{12}$ are independently selected from the group consisting of hydrogen, straight chain or branched lower alkyl containing 1 to 6 carbon atoms, cycloalkyl, aryl, arylalkyl, halogen, and alkoxy; or more preferably M is SiMe₃ as described by H. Sakurai in Pure & Appl. Chem., 54, 1 (1982), or SnBu₃; in both cases carrying out the reaction in the presence of an acid such as titanium tetrachloride, to obtain a compound of structure (Va)

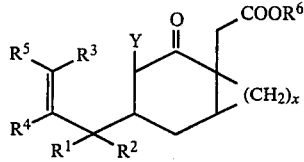
(Va)

wherein R¹, R², R³ R⁴, R⁵, R⁶, Y and x are as defined above and further reacting a compound of structure (Va) with a reducing agent such as sodium dithionite or zinc metal to produce a compound of structure (Vb)

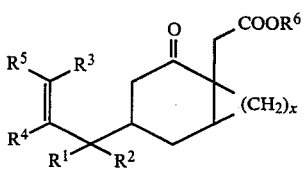
(Vb)

wherein R¹, R², R³, R⁴, R⁵, R⁶ and x are as defined above, and further reacting a compound of structure (Vb) with the substituted hydrazine of formula (VI)

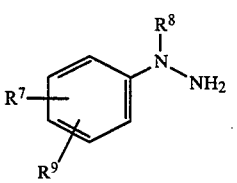
(VI)

wherein R⁷ and R⁹ are hydrogen, lower alkyl, or halogen; R⁸ is hydrogen or lower alkyl to obtain the corresponding hydrazone of structure (VII)

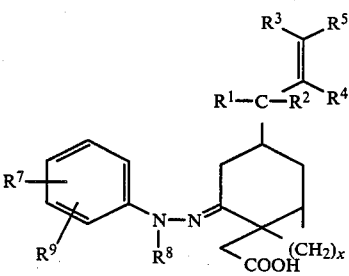
(VII)

wherein R¹, R², R³, R⁴, R⁵, R⁶, R⁷, R⁸, R⁹ and x are as defined above. The hydrazone (VII) is treated with a cyclizing agent to give the ester (XVIII) of compound (I) which is a useful intermediate for the preparation of compound (I); and after hydrolyzing said ester, compound (I) is obtained. The ester (XVIII) of compound (I) wherein R⁹ is acetyl can sometimes be isolated as a minor component of the mixture of reaction products that results from treating hydrazone (VII), wherein R⁹ is H, with a cyclizing agent. Hydrolysis of said ester then produces compound (I) wherein R⁹ is acetyl.

Other compounds of the present invention are prepared by a process in which the unsaturated ketone of structure (IV)

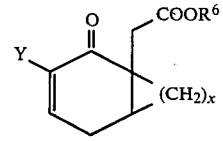
(IV)

wherein R⁶, Y and x are as defined above is reacted with the organometallic reagent

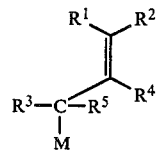

wherein R¹, R², R³, R⁴ and R⁵ are hydrogen or lower alkyl; and M is SiR¹⁰R¹¹R¹² or SnR¹⁰R¹¹R¹² wherein R¹⁰, R¹¹ and R¹² are independently selected from the group consisting of hydrogen, straight chain or branched lower alkyl containing 1 to 6 carbon atoms, cycloalkyl, aryl, arylalkyl, halogen and alkoxy; or more preferrably M is SiMe₃ as described by H. Sakurai in Pure & Appl. Chem., 54, 1 (1982), or SnBu₃; in both cases carrying out the reaction in the presence of an acid such as titanium tetrachloride, to obtain a compound or compounds of structures (Va) or (Vc)

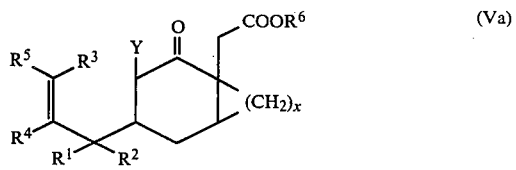
(Va)

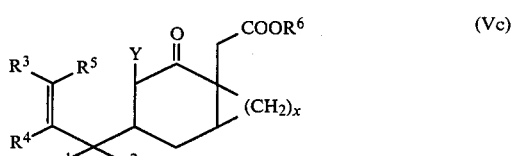
(Vc)

wherein R¹, R², R³, R⁴, R⁵, R⁶, Y and x are as defined above and further reacting a compound of structure (Va) or (Vc) with a reducing agent such as sodium dithionite or zinc metal to produce a compound of structure (Vb) or (Vd)

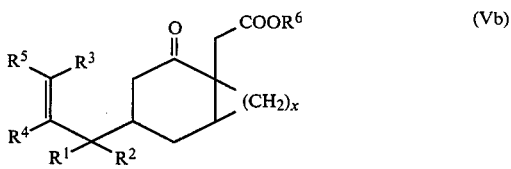
(Vb)

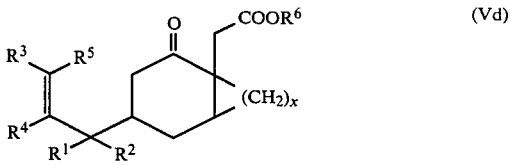
(Vd)

wherein R¹, R², R³, R⁴, R⁵, R⁶ and x are as defined above, and further reacting a compound of structure (Vb) or (Vd) with the substituted hydrazine of formula (VI)

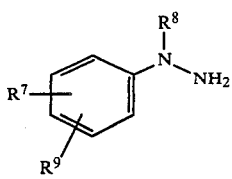

wherein $R^7$, $R^8$ and $R^9$ are as defined above to obtain the corresponding hydrazone of structure (VII)

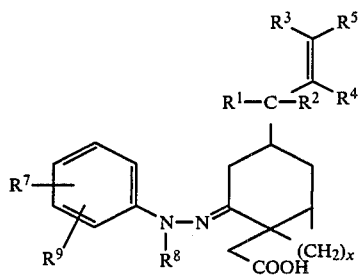

wherein $R^1$, $R^2$, $R^3$, $R^4$, $R^5$, $R^6$, $R^7$, $R^8$, $R^9$ and x are as defined above. The hydrazone (VII) is treated with a cyclizing agent to give the ester (XVIII) of compound (I) which is a useful intermediate for the preparation of compound (I); and after hydrolyzing said ester, compound (I) is obtained. The ester (XVIII) of compound (I) wherein $R^9$ is acetyl can sometimes be isolated as a minor component of the mixture of reaction products that results from treating hydrazone (VII), wherein $R^9$ is H, with a cyclizing agent. Hydrolysis of said ester then produces compound (I) wherein $R^9$ is acetyl.

Other compounds of the present invention are prepared by a process in which the unsaturated ketone of structure (IV)

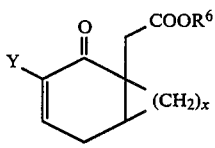

wherein $R^6$, Y and x are as defined above is reacted with the organometallic reagent

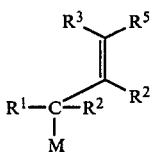

wherein $R^4$ and $R^5$ are joined together to form

—CH=CH—CH=CH—, $R^1$, $R^2$ and $R^3$ are independently hydrogen or lower alkyl; and M is MgBr, MgCl, or MgI, carrying out the reaction in the presence of a suitable copper catalyst selected from the group consisting of copper bromide dimethyl sulfide complex, cuprous iodide, cuprous bromide, copper acetate, cuprous chloride, and tributylphosphine cuprous iodide complex, to obtain a compound of structure (Va)

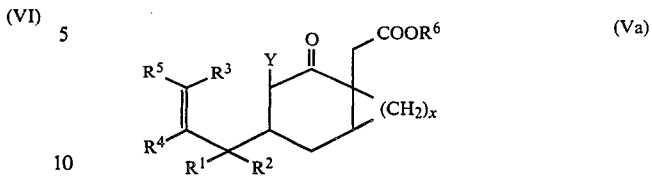

wherein $R^1$, $R^2$, $R^3$, $R^4$, $R^5$, $R^6$, Y and x are as defined above and further reacting a compound of structure (Va) with a reducing agent such as sodium dithionite or zinc metal to produce a compound of structure (Vb)

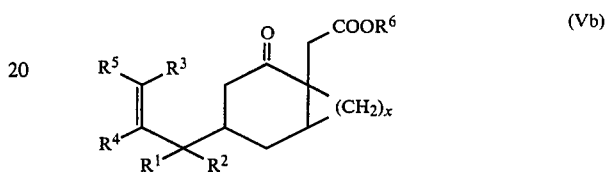

wherein $R^1$, $R^2$, $R^3$, $R^4$, $R^5$, $R^6$ and x are as defined above, and further reacting a compound of structure (Vb) with the substituted hydrazine of formula (VI)

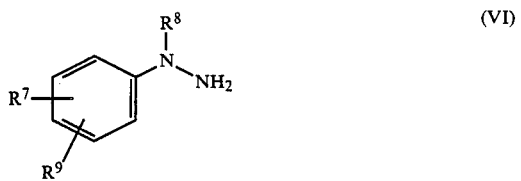

wherein $R^7$, $R^8$ and $R^9$ are as defined above to obtain the corresponding hydrazone of structure (VII)

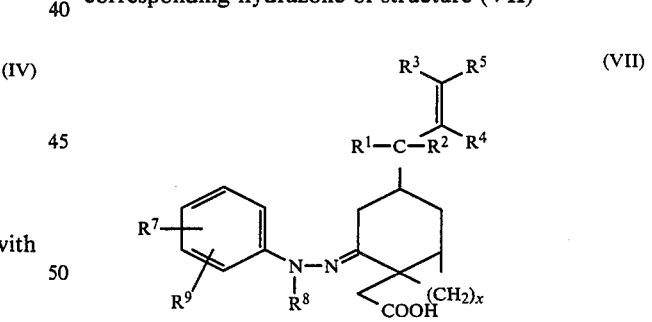

wherein $R^1$, $R^2$, $R^3$, $R^4$, $R^5$, $R^6$, $R^7$, $R^8$, $R^9$ and x are as defined above. The hydrazone (VII) is treated with a cyclizing agent to give the ester of compound (I) which is a useful intermediate for the epreparation of compound (I); and after hydrolyzing said ester, compound (I) is obtained. The ester (XVIII) of compound (I) wherein $R^9$ is acetyl can sometimes be isolated as a minor component of the mixture of reaction products that results from treating hydrazone (VII), wherein $R^9$ is H, with a cyclizing agent. Hydrolysis of said ester then produces compound (I) wherein $R^9$ is acetyl.

Other compounds of the present invention are prepared by a process in which the ketone of structure (VIII)

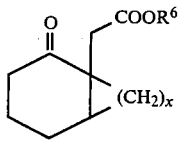
(VIII)

wherein $R^6$ is lower alkyl containing 1 to 6 carbon atoms and x is 1 to 5, is treated with the substituted hydrazine of formula (VI)

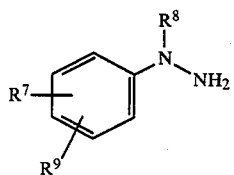
(VI)

wherein $R^7$, $R^8$ and $R^9$ are as defined above to obtain the corresponding hydrazone of structure (IX)

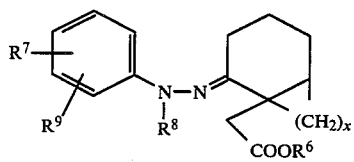
(IX)

wherein $R^6$, $R^7$, $R^8$, $R^9$ and x are as defined above. The hydrazone (IX) is treated with a cyclizing agent to give the ester (XIX) of compound (Ia) which is a useful intermediate for the preparation of compound (Ia), and after hydrolyzing said ester, compound (Ia) is obtained. The ester (XIX) of compound (Ia) wherein $R^9$ is acetyl can sometimes be isolated as a minor component of the mixture of reaction products that results from treating hydrazone (IX), wherein $R^9$ is H, with a cyclizing agent. Hydrolysis of said ester then produces compound (Ia) wherein $R^9$ is acetyl.

The starting material of formula (Vb), (Vd) or (VIII) is condensed with substantially one molar equivalent of the starting material of formula (VI) to give the corresponding hydrazone of formula (VII) or (IX) in which $R^1$ to $R^9$ inclusive and x are as defined hereinbefore. The condensation to form hydrazones (VII) or (IX) is performed preferably in an inert atmosphere, for example, nitrogen or argon. The condensation can be carried out in the absence of a solvent, but if desired, a suitable solvent may be selected from the group consisting of the lower alkanols such as methanol and ethanol; aromatics such as benzene and toluene; the ethers, such as tetrahydrofuran, diethyl ether, dioxane, bis(2-methoxyethyl)-ether and the like; and the halogenated hydrocarbons, methylene chloride, chloroform and the like. Methanol, ethanol and toluene are practical solvents. Times and temperatures for the condensation generally range from 5 minutes to five or six days at 0° to 100° C. Convenient time and temperature ranges include 20° C. to the boiling point of the mixture and 15 minutes to 130 hours. Preferably, the reaction is run without solvent.

The resulting hydrazone (VII) or (IX) is then cyclized to the tetracyclic ester of formula (I) or (Ia), respectively, by the action of a suitable cyclization agent according to the conditions of the "Fischer Indole Synthesis," for example, see B. Robinson, Chem. Rev. 63, 373 (1963).

A variety of cyclization agents are effective for this cyclization, some of the agents suitable for this cyclization include p-toluenesulfonic acid, hydrogen chloride or hydrogen chloride generated from acetyl chloride, hydrogen bromide, phosphoric acid, sulfuric acid, aluminum chloride, zinc chloride, hydrogen bromide in acetic acid, boron trifluoride-etherate, trifluoroacetic acid, cationic ion exchange resins such as Amberlite IR-120, phenyl or ethyl magnesium bromide ad aniline salts. In other words the usual catalysts employed for the "Fischer Indole Synthesis" are efficacious; however, the preferred cyclization agent is a solution of boron trifluoride etherate in acetic acid.

In practice the isolation of the hydrazone (VII) or (IX) from the condensation reaction mixture is optional. Accordingly, the cyclization agent is added either to the above condensation reaction mixture containing the hydrazone, or to the isolated hydrazone optionally dissolved in one of the above solvents, whereby the hydrazone then cyclizes to give the corresponding tetracyclic ester of formula (I) or (Ia) in which $R^1$ to $R^9$ inclusive and x are as defined hereinbefore.

The cyclization usually proceeds smoothly and rapidly. Convenient reaction times for the cyclization include five minutes to two hours, preferably 30 minutes to one hour. Convenient temperatures include 20° to 200° C., preferably 120° to 180° C.

In practice a most convenient and practical procedure for effecting the above cyclization comprises evaporating solvent from the condensation reaction mixture containing the hydrazone if a solvent was used, and then heating the hydrazone at reflux in a solution of boron trifluoride etherate in acetic acid.

The starting material of formula (Vb), (Vd) or (VIII) may be either a cycloalkanoneacetic acid derivative or its corresponding lower alkyl ester ($R^6$=lower alkyl). Accordingly, when the acid is employed, the above process yields the tetracyclic compound identical to the desired compound of formula (I) or (Ia), and when the starting material is lower alkyl ester the above process yields the lower alkyl ester tetracyclic compound of formula (I) or (Ia).

The subsequent conversion of the lower alkyl ester tetracyclic compound of formula (I) or (Ia) to the corresponding compound of formula (I) or (Ia) is effected readily by subjecting the tetracyclic compound to hydrolysis. Generally speaking, this conversion is most conveniently performed by employing a base as the hydrolyzing agent. The hydrolysis is performed in the presence of sufficient water optionally under an inert atmosphere, followed by acidification of the reaction mixture to yield the desired compound of formula (I) or (Ia). However, the manner of hydrolysis is not intended to be limited to basic hydrolysis since hydrolysis under acidic conditions and other variations, for example, treatment with lithium iodide in collidine (see L. F. Fieser and M. Fieser, "Reagents for Organic Synthesis," John Wiley and Sons, Inc., New York, 1967, (pp. 615–617) are also applicable.

For basic hydrolysis a preferred embodiment involves subjecting the tetracyclic ester to the action of a base, for example, sodium or potassium carbonate, in the presence of sufficient water to effect hydrolysis of the ester. The hydrolysis is performed using a suitable solvent, for example, methanol or ethanol under a nitrogen atmosphere.

The reaction mixture is maintained at a temperature of from 25° C. to the reflux temperature until hydrolysis occurs. Usually from 10 minutes to 48 hours is sufficient for this hydrolysis. The reaction mixture is then rendered acidic with an acid, for example, acetic acid, hydrochloric acid, sulfuric acid and the like, to release the free acid as a solid.

Alternatively, the tetracyclic ester is hydrolyzed by subjecting the ester to the action of a hydrolyzing agent which is a strong organic or inorganic acid, for example, trifluoroacetic acid, p-toluenesulfonic acid, hydrochloric acid, hydrobromic acid, hydroiodic acid, sulfuric acid, phosphoric acid and the like in a suitable solvent at a temperature of at least 60° C. and preferably from 90° C. to the boiling point of the mixture until the hydrolysis occurs. Usually from 5 to 48 hours are required for this hydrolysis. Suitable solvents include water, acetic acid, aqueous alcohols and the like. In acid hydrolysis is used, the free acid is formed directly. If necessary, the reaction mixture can be diluted with water to precipitate the product.

The requisite starting materials of formula (VI), phenylhydrazine or substituted phenylhydrazines are known or are prepared according to known methods. A convenient method for preparing the substituted phenylhydrazines involves the diazotization of the appropriately substituted aniline to give the corresponding diazo derivative. The latter compound is then reduced with stannous chloride or sodium sulfite to give the corresponding phenylhydrazine, see L. F. Fieser and M. Fieser, "Advanced Organic Chemistry," Reinhold Publishing Corporation, New York, 1961, p. 734.

The starting materials of formula (IV)

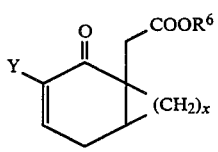

(IV)

wherein $R^6$, Y and x are as defined above is obtained from a compound of formula (VIII)

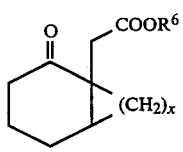

(VIII)

wherein $R^6$ and x are as defined above by treating (VIII) with a halogenating agent such as bromine, cupric bromide, or sulfuryl chloride in a suitable solvent such as methylene chloride, chloroform, methanol, diethyl ether, or acetic acid to produce the novel intermediate compound (X)

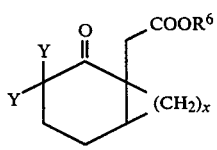

(X)

wherein $R^6$, Y and x are as defined above, and dehydrohalogenating compound (X) in the presence of a base such as lithium carbonate, calcium carbonate, diazabicycloundecane, or collidine with or without added salts such as lithium bromide, or sodium chloride in a suitable solvent such as N,N-dimethylformamide, or dimethylsulfoxide to produce the novel intermediate compound (IV).

The starting material of formula (VIII)

(VIII)

wherein $R^6$ is lower alkyl and x is 2, can be prepared from ketone (XI)

(XI)

wherein $R^6$ is as defined above, prepared as described by Ziegler et al, in J. Am. Chem. Soc., 104, 7181–7190 (1982), by irradiating (XI) with ultra violet light in the presence of ethylene in an inert solvent at a temperature from −100° C. to 0° C. Preferably, the irradiation is carried out through a pyrex filter using methylene chloride as the solvent at a temperature of −78° C. to −40° C. This affords a compound of formula (VIII) wherein x is 2 and $R^6$ is lower alkyl.

The starting materials of formula (VIII)

(VIII)

wherein $R^6$ is lower alkyl and x is 1, can be prepared from ketone (XI)

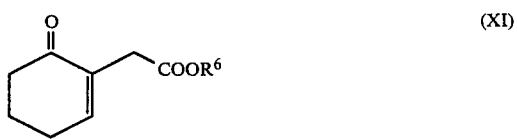

(XI)

wherein $R^6$ is lower alkyl, by cyclopropanating the double bond. This is easily accomplished with sodium hydride and trimethylsulfoxonium iodide as described by Corey et al, in J. Am. Chem. Soc., 87, 1353–1364 (1965), which leads directly to (VIII) wherein x is 1 and $R^6$ is lower alkyl.

The starting material of formula (VIII)

(VIII)

wherein $R^6$ is lower alkyl and x is 3 to 5, can be prepared from ketone (XI)

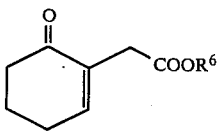
(XI)

wherein $R^6$ is lower alkyl, by treatment with a suitable protected organometalic reagent such as (XII)

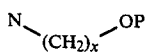
(XII)

wherein x is 3 to 5, N is a metal group such as MgBr, MgCl, MgI, Li, Cu, CuCNLi; P is an alcohol protecting group such as

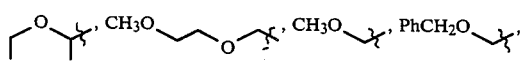

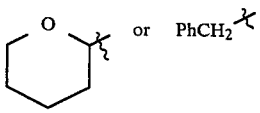

The reaction may be done in the presence of a copper catalyst when N does not contain copper, such as copper bromide dimethyl sulfide complex, cuprous iodide, cuprous bromide, copper acetate, cuprous chloride and tributylphosphine cuprous iodide complex. Illustrations of this reaction can be found in C-T Hsu et al, J. Am. Chem. Soc., 105, 593–601 (1983) and B. H. Lipshutz, Synthesis, 325–341 (1987). This affords a compound of formula (XIII)

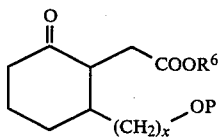
(XIII)

wherein $R^6$, x, and P are as defined above. The protecting group P is removed under suitable conditions such as acid hydrolysis for acetal protecting groups or reduction for protecting groups containing a $PhCH_2O$ group, affording a compound of formula (XIV)

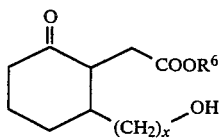
(XIV)

wherein x and $R^6$ are as defined above. The alcohol group in compound (XIV) is then converted to a leaving group Z affording a compound of formula (XV)

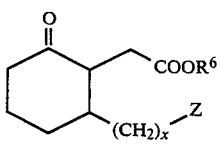
(XV)

wherein $R^6$ and x are as defined above and Z is selected from the group consisting of chlorine, bromine, iodine, $MeSO_3$, $ArSO_3$ (Ar may be phenyl paramethylphenyl, para-bromophenyl or para-nitrophenyl). In the case of Z is $MeSO_3$ or $ArSO_3$, the transformation may be carried out by treating a methylene chloride solution of (XIV) with $MeSO_2Cl$ or $ArSO_2Cl$ in the presence of an amine such as triethylamine which would lead directly to (XV). In the case of Z is chlorine, bromine or iodine, the compound can be made directly from (XV) wherein Z is $MeSO_3$ or $ArSO_3$ by treatment with an appropriate halogen salt such as LiBr, NaBr, LiCl or NaI in an inert solvent such as acetone, tetrahydrofuran, or $Me_2N$-CHO.

Compound (XV) can then by cyclized to compound (VIII) wherein x is 3 to 5 and $R^6$ is lower alkyl, by treatment with an appropriate base such as $Me_3COK$. Illustration of such a cyclization can be found in E. Piers et al, Can. J. Chem., 57, 1064–1074 (1979) and A. G. Shultz et al, J. Org. Chem., 48, 2318–2321 (1983).

Compounds of formula (I) or (Ia) wherein $R^8$ is lower alkyl can also be prepared by treating an ester of compound (I), wherein $R^8$ is H, with sodium hydride or potassium hydride in a suitable solvent followed by treatment with an alkyl halide followed by hydrolysis of the ester.

Also included in the present invention are optically active compounds of formula (XVI)

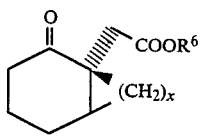
(XVI)

wherein $R^6$ and x are as defined above; and optically active compounds of formula (XVII)

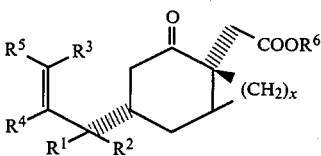
(XVII)

wherein $R^1$, $R^2$, $R^3$, $R^4$, $R^5$, $R^6$ and x are as defined above.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl, hexyl, and the like.

The term "halogen" as used herein includes fluorine, chlorine, bromine and iodine.

The compounds of formula (I) and (Ia) form salts with suitable pharmaceutically acceptable inorganic and organic bases. These derived salts possess the same activity as the parent acid and are included within the scope of this invention. The acid of formula (I) or (Ia) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates, or alkoxides of the alkali metals or alkaline earth metals, for example, sodium potassium, magnesium, calcium, and the like. Suitable organic bases include the following amines; lower mono-, di- and tri-alkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; amino sugars, such as glucosamine; phenyl substituted alkylamines, such as benzenemethanamine or N,N′-bis-(phenylmethyl)-1,2-ethanediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethyl-piperidinium salts, which are characterized by good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) or (Ia) in water containing at least one equivalent amount of a hydroxide, carbonate, or bicarbonate corresponding to the inorganic salt desired. Advantageously, the reaction is performed in a water-miscible organic solvent inert to the reaction conditions, for example, methanol, ethanol, dioxane, and the like in the presence of water. For example, such use of sodium hydroxide, sodium carbonate, or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acid of formula (I) or (Ia) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) or (Ia) with an equivalent amount of the corresponding quaternary ammonium hydroxide in water solution, followed by evaporation of the water.

Included in the present invention are the diastereomers wherein the substituent at the starred carbon in the saturated ring of compound (XX) is either cis or trans to the acetic acid chain, or wherein the acetic acid chain is either cis or trans to the methine hydrogen on the tertiary carbon atom adjacent to the carbon atoms bearing the acetic acid chain.

Also included in this invention are the optical isomers of the compounds of formula (I) or (Ia) which result from asymmetric centers, contained therein. Such isomers are obtained in substantially pure form by classical separation techniques and by sterically controlled synthesis.

The compounds of the invention, by virtue of their ability to inhibit the activity of lipoxygenase enzyme and/or cyclooxygenase enzyme are useful in the treatment of inflammatory and painful conditions. Accordingly, the compounds are indicated in the treatment of such diseases as rheumatoid arthritis, osteoarthritis, tendinitis, bursitis and similar conditions involving inflammation. Moreover, by virtue of their ability to inhibit the activity of lipoxygenase enzyme they are useful for the inhibition of symptoms induced by leukotrienes. Accordingly, the compounds are indicated in the prevention and treatment of those disease states in which $LTC_4$, $LTD_4$ and $LTE_4$ are causative factors, for example allergic rhinitis, allergic bronchial asthma and other leukotriene mediated naso-bronchial obstructive airpassageway conditions, as well as in other immediate hypersensitivity reactions, such as allergic conjunctivitis. The compounds are especially valuable in the prevention and treatment of allergic bronchial asthma.

When the compounds of the invention are employed in the treatment of allergic airway disorders and/or as anti-inflammatory agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least sufficient to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can be utilized in the form of an aerosol.

The dosage requirements vary with the particular compositions employed, the route of administration, the severity of the symptoms presented and the particular subject being treated. Treatment will generally be initiated with dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day. These effective concentration levels are usually obtained within a therapeutic range of 1.0 μg to 500 mg/kg per day, with a preferred range of 10 μg to 100 mg/kg per day.

The lipoxygenase inhibitory effects as well as the anti-inflammatory effects of the compounds of the invention may be demonstrated by standard pharmacological procedures, which are described more fully in the examples given hereinafter.

ANTI-INFLAMMATORY ACTIVITY

The useful anti-inflammatory activities of the fused tetrahydrocarbozole acetic acid derivatives of formula (I) and (Ia) are demonstrated in standard pharmacologic tests, for example, the test designated: Preventative Adjuvant Edema.

The objective of this test is to determine the ability of test drugs to exhibit an acute anti-inflammatory effect in rats. This test is a primary screen for anti-inflammatory drugs.

Species:

Male Sprague Dawley rates (180–200 g) are used. The animals have free access to water but food is withdrawn 18 hours before testing.

Drug Preparations and Administration:

Freund's complete adjuvant is prepared by suspending 5 mg of killed and dried *Mycobacterium butyricum* (Difco) in 1 mL liquid paraffin. The test compounds are dissolved in distilled water or suspended in 0.5% Tween 80 in distilled water according to their solubility. For primary screening all drugs are administered by gastric lavage at the arbitrary dosage of 25 mg/kg, p.o. in a volume of 0.5 mL/100 g body weight to groups of 10 animals.

Methodological Details:

The method is essentially that described by Wax et al. J. Pharmacol. Exp. Ther., 192, 166–171 (1975). Groups of rats are injected intradermally in the left hind paw with 0.1 mL of Freund's complete adjuvant. The test compound or vehicle is administered immediately before the adjuvant, 24 hours and 48 hours after the adjuvant (days 0, 1 and 2). The injected hind paw volume is measured before the injection of adjuvant and 24 hours after the last drug administration (day 3) by means of a plethysmometer (Buxco Electronics Inc.). The difference between the hind paw volume on day 0 and day 3 represents the edema volume. Etodolac (25 mg/kg, p.o.) is included as a positive control.

Presentation of Results:

The mean edema volume (expressed as mL±SEM) is calculated for each group and the percentage inhibition of inflammation conferred by the drug is calculated:

$$\% \text{ inhibition} = \left[ \frac{(c - t)}{c} \right] \times 100$$

where c is the mean edema volume for the untreated controls and t is the mean edema volume for the drug treated group.

ANALGESIC ACTIVITY

A further test used to determine the utility of the compounds of the present invention is designated: Drug Effects on Phenylbenzoquinone-induced Writhing in Mice The objective of this test is to determine the ability of test drugs to inhibit the nociceptive (pain) response of mice injected with a chemical irritant. This test is a primary screen for both peripheral and centrally acting analgesic drugs.

Species:

Male Swiss albino mice (15–25 g) are used. The animals are fasted for 18 hours prior to use but have free access to water.

Drug Preparation and Administration:

Drugs are dissolved or suspended according to their solubility in 0.5% Tween 80 in distilled water. They are administered by gastric gavage in a volume of 5 mL/kg. For primary screening all drugs are administered at the arbitary dosage of 25 mg/kg, p.o. to a group of 10 mice.

Methodological Details:

A modification of the method of Siegmund et al, Proc. Soc. Exp. Biol. Med., 95, 729–731 (1957) is used. Groups of 5 mice are dosed with the test compound or vehicle control. Sixty minutes later the animals are injected i.p. with 0.3 mL/20 g body weight of a 0.02% solution of phenylbenzoquinone (PBQ; 2-phenyl-1,4-benzoquinone) and placed in individual observation boxes. The number of writhing or abdominal squirming movements made by each mouse during the following 15 minute period is counted. The experiment is repeated with another group of 5 mice and the mean number of writhes per mouse for a group of 10 mice is calculated.

Presentation of Results:

Drug treated and vehicle-treated control groups are compared and the percentage inhibition of writhing conferred by the drug is calculated:

$$\% \text{ inhibition} = \left[ \frac{(c - t)}{c} \right] \times 100$$

where c=mean number of writhes in the control group where t=mean number of writhes in the test drug group A test for lipoxygenase and cyclooxygenase inhibitory activity is the Rat Polymorphonuclear Leukocyte Assay. The assay is carried out as follows: glycogen-elicited rat peritoneal cells ($10^7/1.0$ mL) are incubated (37° C.)±drug in a shaking water bath for 10 minutes. One micromolar (final concentration) $^3$H arachidonic acid (2.0 μCi) is then added to each sample followed by the immediate addition of 1.0 micro-molar A23187* (final concentration). The cells are incubated another 10 minutes and the reaction is stopped by high-speed centrifugation. Supernatants are then analyzed by HPLC using an in-line radioactivity detector. Effective drugs demonstrate a reduction in the integrated value of a given eicosanoid peak. Results are qualitatively expressed as a percent change (minus=decrease, plus=increase) relative to the control (no drug).

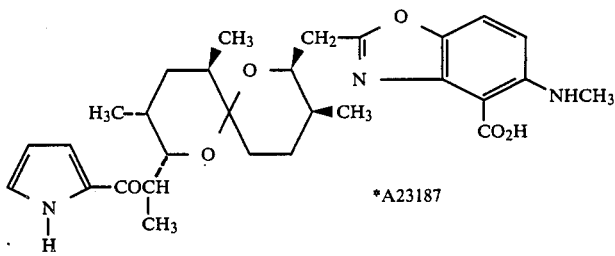

*A23187

Typical results obtained for the compounds of the present invention in the aforementioned tests are as follows:

| Preventative Adjuvant Edema | |
|---|---|
| Example 1 | 26% inhibition at 25 mg/kg, p.o. |
| Example 2 | 85% inhibition at 25 mg/kg, p.o. |
| Example 4 | 64% inhibition at 25 mg/kg, p.o. |
| Example 6 | 13% inhibition at 25 mg/kg, p.o. |

| Phenylbenzoquinone Writhing in Mice | |
|---|---|
| Example 1 | 73% inhibition at 10 mg/kg, p.o. |
| Example 2 | 56% inhibition at 10 mg/kg, p.o. |
| Example 4 | 21% inhibition at 10 mg/kg, p.o. |
| Example 5 | 56% inhibition at 10 mg/kg, p.o. |
| Example 6 | 27% inhibition at 10 mg/kg, p.o. |
| Example 7 | 0% inhibition at 10 mg/kg, p.o. |

| Rat Polymorphonuclear Leukocyte Assay | | | |
|---|---|---|---|
| % change at 10 | | M drug concentration | |
| leukotriene B4 | 5-HETE* | thromboxane B2 | prostaglandin E2 |
| Example 5 | +80 | +87 | −86 | −77 |
| Example 7 | −93 | −78 | −99 | −99 |

*5-hydroxyeicosatetraenoic acid

The lack of side effects for the compounds of this invention are demonstrated by standard acute toxicity tests described by R. A. Turner in "Screening Methods in Pharmacology," Academic Press, New York and London, 1965, pp. 152–163 and by prolonged administration of the compound to warm-blooded animals.

The compounds of this invention also possess antipyretic activity.

The following examples further illustrate this invention.

EXAMPLE 1 cis-7-Chloro-1,2,2a,3,4,9-hexahydro-8-methyl-4-(phenylmethyl)-9bH-cyclobuta[a]carbazole-9b-acetic Acid (Step 1) Preparation of cis-2-Oxobicyclo[4.2.0]octane-1-acetic Acid Ethyl Ester 6-Oxo-1-cyclohexeneacetic acid ethyl ester (21.3 g, 1.27 mmol) prepared by the process of Ziegler et al, J. Am. Chem. Soc., 104, 7181 (1982), was dissolved in CH$_2$Cl$_2$ (enough to fill the vessel) and the reaction mixture was transferred to a quartz photochemical reactor. The reaction vessel was then cooled to −78° C. and the solution was saturated with ethylene gas. Finally, the UV light source (Conrad-Hanovia 450 watts) was allowed to irradiate the reaction mixture for 3 weeks affording 3.2 g (15%) of product and 7.3 g of starting material.

(Step 2) Preparation of cis-3,3-Dibromo-2-oxobicyclo[4.2.0]octane-1-acetic Acid Ethyl Ester cis-2-Oxobicyclo[4.2.0]octane-1-acetic acid ethyl ester (9.37 g, 44.69 mmol) was dissolved in 100 mL of methylene chloride and treated dropwise with a solution of bromine (4.59 mL, 89.38 mmol) in 40 mL of methylene chloride at room temperature under nitrogen. The reaction mixture was then washed with 100 mL of saturated sodium sulfite. The organic phase was then dried over MgSO$_4$ and concentrated in vacuo affording 14.16 g (86%) of product.

(Step 3) Preparation of cis-3-Bromo-2-oxobicyclo[4.2.0]oct-3-ene-1-acetic Acid Ethyl Ester cis-3,3-Dibromo-2-oxobicyclo[4.2.0]octane-1-acetic acid ethyl ester (14.16 g) lithium bromide (4.88 g, 56.21 mmol), and lithium carbonate (2.98 g, 14.4 mmol) were dissolved in 47.3 mL of DMF under nitrogen and heated to 100° C. for 5 minutes. The reaction mixture was then poured into 500 mL of water and extracted with 4×100 mL of toluene. The organic phase was washed with 4×100 mL of water, dried over MgSO$_4$, and concentrated in vacuo affording 8.86 g (80%) of product.

(Step 4) Preparation of cis-3-Bromo-2-oxo-4-(phenylmethyl)bicyclo[4.2.0]octane-1-acetic Acid Ethyl Ester cis-3-Bromo-2-oxobicyclo[4.2.0]oct-3-ene-1-acetic acid ethyl ester (8.86 g, 30.89 mmol) was dissolved in 100 mL of THF at 0° C. under nitrogen and treated with CuBr.Me$_2$S (635 mg, 3.089 mmol), Me$_2$S (9.7 mL), and ZnBr$_2$ (6.95 g, 30.89 mmol) and allowed to stir until all of the zinc bromide had dissolved. Benzyl magnesium chloride (16 mL of 2M solution) was added dropwise to the reaction mixture and left to stir for 1.5 hours. The reaction mixture was then poured into 400 mL of 1N HCl and extracted with 2×250 mL of ether. The combined organic layers were dried over MgSO$_4$ and concentrated in vacuo affording 12.24 g (105%) of product.

(Step 5) Preparation of cis-2-Oxo-4-(phenylmethyl)bicyclo[4.2.0]octane-1-acetic Acid Ethyl Ester cis-3-Bromo-2-oxo-4-(phenylmethyl)bicyclo[4.2.0]octane-1-acetic acid ethyl ester (12.24 g) was dissolved in 63 mL of DMF and 30 mL of water under nitrogen at room temperature and treated with $Na_2S_2O_4$ (15.99 g, 91.84 mmol) then allowed to stir overnight. The reaction mixture was poured into 500 mL of water and extracted with 4×250 mL of 1:1 ether/petroleum ether. The combined organic layers were washed with 1×250 mL of water, 1×250 mL of saturated sodium bicarbonate, and 1×250 mL of brine. The organic phase was then dried over $MgSO_4$ and concentrated in vacuo affording the crude product. Flash chromatography (70 mm column, 10% ethyl acetate/petroleum esther) afforded 3.9 g (41%) of product which consisted largely of one diastereomer.

$^1$H NMR (200 MHz, $CDCl_3$): δ 1.220 (t, 3H, J=7.1 Hz), 1.61–1.68 (m, 2H), 2.04–2.38 (m, 4H), 2.44–2.72 (m, 2H), 2.61–2.67 (m, 4H), 2.65 (d, 1H, J=16.2 Hz), 3.03 (d, 1H, J=16.2 Hz), 4.12 (q, 2H, J=7.1 Hz), 7.15–7.33 (m, 5H).

$^{13}$C NMR (100 MHz, $CDCl_3$): δ 14.08, 20.52, 28.43, 33.43, 33.59, 38.89, 42.87, 43.15, 45.58, 47.45, 60.39, 126.06, 128.26, 129.02, 139.42.

(Step 6) Preparation of cis-7-Chloro-1,2,2a,3,4,9-hexahydro-8-methyl-4-(phenylmethyl)-9bH-cyclobuta[a]carbazole-9b-acetic Acid cis-2-Oxo-4-(phenylmethyl)bicyclo[4.2.0]octane-1-acetic acid ethyl ester (3.64 g, 12.14 mmol) and 3-chloro-2-methylphenylhydrazine (2.1 g, 13.354 mmol) were dissolved in 100 mL of toluene and allowed to reflux overnight under nitrogen with azeotropic removal of water. The toluene was then removed and $BF_3 \cdot Et_2O$ (1.79 mL, 14.57 mmol) and 8.36 mL of acetic acid were added to the residue. The reaction mixture was then allowed to reflux under nitrogen for 30 minutes. The reaction mixture was then poured into 500 mL of water and extracted with 4×100 mL of ether. The combined organic phases were washed with 4×25 mL of 1N HCl, 1×25 mL with 1N NaOH, and 1×25 mL with brine. The organic phase was then dried over $MgSO_4$ and concentrated in vacuo. Flash chromatography (50 mm column, 10% ethyl acetate/petroleum ether as eluant) afforded 2.91 g (57%) of product.

The cis-7-chloro-1,2,2a,3,4,9-hexahydro-8-methyl-4-(phenyl-methyl)-9bH-cyclobuta[a]carbazole-9b-acetic acid ethyl ester was then dissolved in 100 mL of ethanol and 10 mL of 2.5N NaOH and allowed to reflux under nitrogen for 30 minutes. 1N HCl was added to the reaction mixture and the aqueous layer extracted with 2×100 mL of ethyl acetate. The combined organic layers were dried over sodium sulfate and concentrated in vacuo and the residue crystallized from a 4:1 mixture of petroleum ether:benzene affording 1.913 g of product, m.p. 210.5°–215.5° C.

$^1$H NMR (400 MHz, DMSO-d6): δ 1.46–1.69 (m, 3H), 1.96–2.02 (m, 2H), 2.08–2.16 (m, 1H), 2.49 (s, 3H), 2.50–2.55 (m, 2H), 2.83–2.89 (m, 1H), 2.88 (d, 1H, J=14.3 Hz), 3.00 (d, 1H, J=14.3 Hz), 3.17–3.22 (m, 1H), 3.44 (d of d, 1H, J=5.2, 13.0 Hz), 6.88 (d, 1H, J=8.5 Hz), 7.16–7.35 (m, 6H), 10.64 (s, 1H).

IR(KBr): 3400, 3030, 2920, 1690, 1080, 700 cm$^{-1}$.

$^{13}$C NMR (100 MHz, DMSO-d6): δ 14.07, 20.90, 31.31, 32.55, 32.72, 36.33, 38.45, 41.19, 42.40, 113.02, 117.35, 117.66, 118.86, 124.88, 125.11, 125.70, 128.11, 129.07, 136.63, 141.06, 172.72.

Mass spectrum, m/z (Rel. intensity) 393 (M)$^+$, 302 (M-benzyl)$^+$, 91 (benzyl)$^+$.

Anal. Calcd. for $C_{24}H_{24}NO_2Cl$: C, 73.37; H, 5.90; N, 3.56%; Found: C, 73.07; H, 5.63; N, 3.55%.

EXAMPLE 2 cis-7-Chloro-1,2,2a,3,4,9-hexahydro-8-methyl-9bH-cyclobuta[a]carbazole-9b-acetic Acid cis-2-Oxobicyclo[4.2.0]octane-1-acetic acid ethyl ester (3.7 g, 18.87 mmol) prepared by the process of Ziegler et al, J. Am. Chem. Soc., 104, 7181 (1982) and 3-chloro-2-methylphenylhydrazine (2.95 g, 18.87 mmol) were dissolved in 50 mL of toluene and refluxed under nitrogen with azeotropic removal of water for 48 hours. The toluene was removed and 13 mL of acetic acid and 2.78 mL (22.64 mmol) of borontrifluoride etherate was added to the residue. The reaction mixture was then allowed to reflux under nitrogen for 30 minutes. The reaction mixture was then poured into 50 mL of water and extracted with 4×30 mL of ether. The combined organic layers were washed with 4×30 mL of 1N HCl, 1×30 mL of 1N NaOH, and 1×30 mL of brine. The ether layers were dried over $MgSO_4$ and concentrated in vacuo affording 5.7 g of crude product. Flash chromatography (70 mm column, 5% ethyl acetate/petroleum ether eluant) afforded 2.7 g (45%) of cis-7-chloro-1,2,2a,3,4,9-hexahydro-8-methyl-9bH-cyclobuta[a]carbazole-9b-acetic acid ethyl ester.

The ester was dissolved in 22 mL of EtOH and 7 mL of 2.5N NaOH. The solution was refluxed for 30 minutes under nitrogen. The reaction mixture was then acidified with 1N HCl and extracted with 4×50 mL of ethyl acetate. The organic phase was dried over $MgSO_4$ and concentrated in vacuo. Trituration of the resulting thick oil in n-heptane afforded cis-7-chloro-1,2,2a,3,4,9-hexahydro-8-methyl-9bH-cyclobuta[a]carbazole-9b-acetic acid, 1.28 g (50%), m.p. 189°–190° C.

$^1$H NMR (400 MHz, DMSO-d6): δ 1.6–1.88 (m, 5H), 2.27 (m, 1H), 2.52–2.63 (m, 1H), 2.74 (m, 1H), 2.77 (d, 1H, J=14.5 Hz), 2.92 (m, 1H), 2.96 (d, 1H, J=14.4 Hz), 6.96 (d, 1H, J=8.3 Hz), 7.22 (d, 1H, J=8.3 Hz), 10.59 (broad s, 1H), 11.89 (broad s, 1H).

IR (KBr): 3420, 2940, 1700 cm$^{-1}$.

Anal. Calcd. for $C_{17}H_{19}NO_2Cl$: C, 67.21; H, 5.97; N, 4.61%; Found: C, 66.98; H, 6.23; N, 4.58%.

EXAMPLE 3 cis-8-Ethyl-1,2,2a,3,4,9-hexahydro-9bH-cyclobuta[a]carbazole-9b-acetic Acid

According to the procedure of Example 2, cis-2-oxobicyclo[4.2.0]octane-1-acetic acid ethyl ester (3.0 g, 14.29 mmol) was allowed to react with 2-ethylphenylhydrazine (2.137 g, 15.719 mmol) to give 0.645 g (15%) of cis-8-ethyl-1,2,2a,3,4,9-hexahydro-9bH-cyclobuta[a]carbazole-9b-acetic acid ethyl ester as a yellow oil (purified by flash chromatography over $SiO_2$, 7% ethyl acetate/petroleum ether).

$^1$H NMR (200 MHz, $CDCl_3$): δ 1.20 (2t, 6H, J=7.6 Hz), 1.70–2.06 (m, 4H), 2.08–2.57 (m, 2H), 2.60–2.91 (m, 7H), 4.15 (q, 2H, J=7.6 Hz), 6.97–7.22 (m, 2H), 7.37 (d, 1H, 6.9 Hz), 9.21 (s, 1H).

The ester was hydrolyzed according to the procedure of Example 2 to give 0.605 g (overall yield 15%) of cis-8-ethyl-1,2,2a,3,4,9-hexahydro-9bH-cyclobuta[a]-carbazole-9b-acetic acid (purified by flash chromatography on silica gel treated with 2% phosphoric acid-methanol, 5% ethyl acetate/petroleum ether) as a yellow solid. The solid was triturated overnight in n-heptane to give the desired product as a fine white powder, m.p. 170°–171° C.

$^1$H NMR (400 MHz, CDCl$_3$): δ 1.35 (t, 3H, J=7.5 Hz), 1.64–1.88 (m, 4H), 2.10–2.20 (m, 1H), 2.22–2.30 (m, 1H), 2.68–2.93 (m, 7H), 6.99 (d, 1H, J=7.4 Hz), 7.05 (t, 1H, J=7.4 Hz), 7.39 (d, 1H, J=7.4 Hz), 8.9 (br s, 1H)

IR(KBr): 3420, 3500–2500, 1695 cm$^{-1}$.

Anal. Calcd. for C$_{18}$H$_{21}$NO$_2$: C, 76.29; H, 7.47; N, 4.94%; Found: C, 76.23; H, 7.41; N, 4.65%.

EXAMPLE 4 cis-1,2,2a,3,4,9-Hexahydro-9bH-cyclobuta[a]carbazole-9b-acetic Acid cis-2-Oxobicyclo[4.2.0]octane-1-acetic acid ethyl ester (3.5 g, 17.01 mmol) and phenylhydrazine (1.9 mL, 18.8 mmol) were allowed to react according to the procedure of Example 2. Flash chromatography (SiO$_2$, 10% EtOAC/petroleum ether) afforded 0.798 g (16%) of cis-1,2,2a,3,4,9-hexahydro-9bH-cyclobuta[a]carbazole-9b-acetic acid ethyl ester.

The ester was hydrolyzed according to the procedure of Example 2 to give a yellow oil. Flash chromatography of the oil on acid treated silica gel, 20% ethyl acetate/petroleum ether gave 0.376 g (52%) of cis-1,2,2a,3,4,9-hexahydro-9bH-cyclobuta[a]carbazole-9b-acetic acid as a yellow oil which was triturated in n-heptane to give a white powder (0.3 g, 42%), m.p. 150°–152° C.

$^1$HNMR (400 MHz, CDCl$_3$): δ 1.79–1.89 (m, 4H), 2.10–2.18 (m, 1H), 2.21–2.26 (m, 1H), 2.68–2.75 (m, 2H), 2.87–2.91 (m, 1H), 2.92 (s, 2H), 7.09 (dt, 1H, J=7.4 Hz, 0.9 Hz), 7.15 (dt, 1H, J=7.6 Hz, 1.2 Hz), 7.33 (d, 1H, J=8.0 Hz), 7.54 (d, 1H, J=7.8 Hz), 8.81 (br s, 1H).

IR(KBr): 3440, 3060, 3500–2500, 1700 cm$^{-1}$.

Anal. Calcd. for C$_{16}$H$_{17}$NO$_2$: C, 75.27; H, 6.71; N, 5.49%; Found: C, 75.16; H, 6.73; N, 5.35%.

EXAMPLE 5 cis-6-Acetyl-1,2,2a,3,4,9-hexahydro-8-propyl-9bH-cyclobuta[a]carbazole-9b-acetic Acid cis-2-Oxobicyclo[4.2.0]octane-1-acetic acid ethyl ester (3.55 g, 16.9 mmol) and n-propylphenydrazine (2.79 g, 18.59 mmol) were allowed to react according to the procedure of Example 2. Flash chromatography of the crude mixture (95 mm column, SiO$_2$, eluted with 10% ethyl acetate/petroleum ether) gave 0.894 g (16%) of cis-6-acetyl-1,2,2a,3,4,9-hexahydro-8-propyl-9bH-cyclobuta[a]carbazole-9b-acetic acid ethyl ester as a yellowish solid.

The ethyl ester was hydrolyzed according to the procedure of Example 2 to give a yellow solid. Flash chromatography of the solid on acid treated silica gel (2% H$_3$PO$_4$ in methanol, 20% ethyl acetate/petroleum ether eluant) gave cis-6-acetyl-1,2,2a,3,4,9-hexahydro-8-propyl-9bH-cyclobuta[a]carbazole-9b-acetic acid 0.35 g (37%) as a yellow solid. Trituration of this material in n-heptane/1 mL of ethyl acetate gave 0.2 g (21%) of a creamy fine solid, m.p. 203°–205° C.

$^1$H NMR (400 MHz, DMSO-d6): δ 0.95 (t, 3H, J=7.3 Hz), 1.16–1.98 (m, 7H), 2.28 (q, 1H, J=10 Hz), 2.57 (s, 3H), 2.64–2.66 (m, 1H), 2.77–2.87 (m, 4H), 2.93–2.98 (m, 2H), 7.48 (d, 1H, J=1.5 Hz), 7.96 (d, 1H, J=1.5 Hz), 10.81 (br s, 1H), 11.95 (br s, 1H).

IR(KBr): 3330, 3600–2500, 1710, 1650 cm$^{-1}$.

MS, m/e (M$^+$) 339 (36), (M$^+$—CH$_2$=CH$_2$) 311 (100).

EXAMPLE 6

(1a.α,8b.α)-7-Ethyl-1,1a,2,3,8,8b-hexahydrocyclopropa[a]carbazole-8b-acetic Acid (Step 1) Preparation of 2-Oxobicyclo[4.1.0]heptane-1-acetic Acid Ethyl Ester Sodium hydride (18.1 mmol, 543 mg of an 80% dispersion in mineral oil) was washed with 2×5 mL of petroleum ether under nitrogen, then it was dried and trimethylsulfoxonium iodide (3.99 g, 18.1 mmol) was added to the flask followed by 21.6 mL dimethylsulfoxide added dropwise. Next, a solution of 6-oxo-1-cyclohexeneacetic acid ethyl ester (2.90 g, 17.3 mmol) was added dropwise as a solution in 4.5 mL of dimethylsulfoxide as the reaction mixture was cooled with a water bath. After the addition, the reaction mixture was stirred at room temperature for 1.5 hours then poured into 80 mL of cold water and extracted with 4×60 mL of ether. The extracts were combined, washed with 80 mL of brine, dried over magnesium sulfate and concentrated affording 2.4 g (13.2 mmol, 73% yield) of the title compound as a yellow oil.

IR(neat): 3020, 2960, 2880, 1730, 1680 cm$^{-1}$.

(Step 2) Preparation of (1a.α,8b.α)-7-Ethyl-1,1a,2,3,8,8b-hexahydrocyclopropa[a]-carbazole-8b-acetic Acid The title compound was prepared from 2-oxobicyclo[4.1.0]heptane-1-acetic acid ethyl ester by a Fisher indole reaction with 2-ethylphenylhydrazine followed by ester hydrolysis as described in Example 1, Step 6, m.p. 154°–156° C. (foams).

IR(KBr): 3410, 3040, 3000, 2960, 2900, 2840, 1685 cm$^{-1}$.

Anal. Calcd. for C$_{17}$H$_{19}$NO$_2$: C, 75.81; H, 7.11; N, 5.20%; Found: C, 76.19; H, 6.83; N, 5.09%.

EXAMPLE 7 cis-1,2,2a,3,4,9-Hexahydro-4-(phenylmethyl)-9bH-cyclobuta[a]carbazole-9b-acetic Acid The title compound (m.p. 117°–119.7° C.) was prepared as described in Example 1 by substituting phenylhydrazine for 3-chloro-2-methylphenylhydrazine.

We claim:

1. A compound of formula (I)

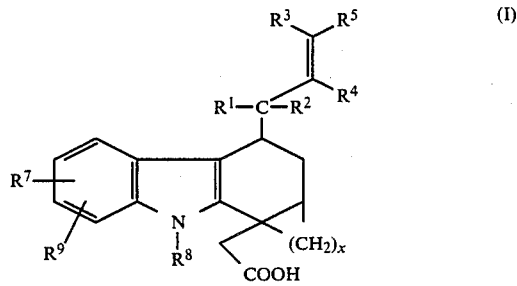

wherein R$^1$, R$^2$, R$^3$, R$^4$ and R$^5$ are independently hydrogen or lower alkyl containing 1 to 6 carbon atoms; or $R^1$ and $R^3$ are joined together to form $(CH_2)_m$; or $R^4$ and $R^5$ are joined together to form —CH=CH—CH=CH—, or $(CH_2)_n$ $R^7$ is hydrogen, lower alkyl containing 1 to 6 carbon atoms or halogen; $R^8$ is hydrogen or lower alkyl containing 1 to 6 carbon atoms; $R^9$ is hydrogen, lower alkyl containing 1 to 6 carbon atoms, halogen, or acetyl; m is 2 to 3; n is 2 to 4, and x is 1 to 5; and the pharmaceutically acceptable salts thereof.

2. A compound of formula (II)

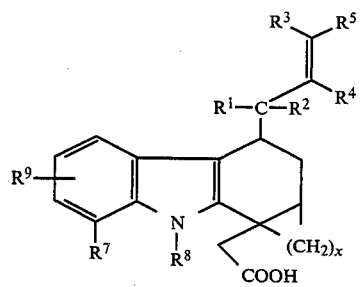

wherein $R^1$, $R^2$, $R^3$, $R^4$ and $R^5$ are independently hydrogen or lower alkyl containing 1 to 6 carbon atoms; or $R^1$ and $R^3$ are joined together to form $(CH_2)_3$; or $R^4$ and $R^5$ are joined together to form —CH=CH—CH=CH—, or $(CH_2)_4$, $R^7$ is hydrogen, lower alkyl containing 1 to 6 carbon atoms, or halogen; $R^8$ is hydrogen or lower alkyl containing 1 to 6 carbon atoms; $R^9$ is hydrogen, lower alkyl containing 1 to 6 carbon atoms, halogen, or acetyl; x is 1 to 5; and the pharmaceutically acceptable salts thereof.

3. A compound of formula (III)

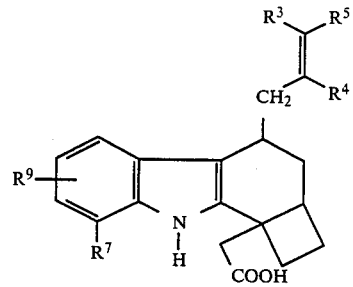

wherein $R^3$, $R^4$ and $R^5$ are hydrogen; or $R^4$ and $R^5$ are joined together to form —CH=CH—CH=CH—; $R^7$ is hydrogen, methyl, ethyl, or propyl; $R^9$ is hydrogen, halogen or acetyl; and the pharmaceutically acceptable salts thereof.

4. The compound according to claim 3 designated cis-7-chloro-1,2,2a,3,4,9-hexahydro-8-methyl-4-(phenylmethyl)-9bH-cyclobuta[a]carbazole-9b-acetic acid and the pharmaceutically acceptable salts thereof.

5. The compound according to claim 3 designated cis-1,2,2a,3,4,9-hexahydro-4-(phenylmethyl)-9bH-cyclobuta[a]carbazole-9b-acetic acid and the pharmaceutically acceptable salts thereof.

6. A compound of formula (XVIII)

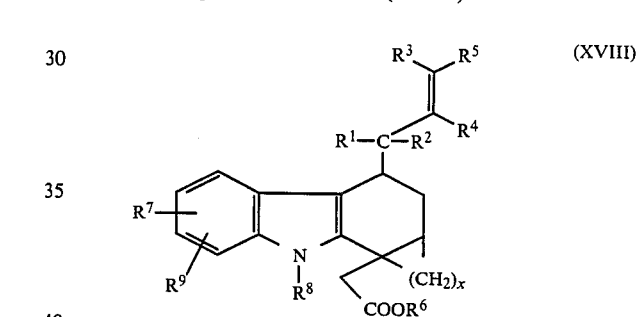

wherein $R^1$, $R^2$, $R^3$, $R^4$, and $R^5$ are independently hydrogen or lower alkyl containing 1 to 6 carbon atoms; or $R^1$ and $R^3$ are joined together to form $(CH_2)_m$; or $R^4$ and $R^5$ are joined together to form —CH=CH—CH=CH—, or $(CH_2)_n$ $R^6$ is lower alkyl containing 1 to 6 carbon atoms; $R^7$ is hydrogen, lower alkyl containing 1 to 6 carbon atoms or halogen; $R^8$ is hydrogen or lower alkyl containing 1 to 6 carbon atoms; $R^9$ is hydrogen, lower alkyl containing 1 to 6 carbon atoms, halogen, or acetyl; m is 2 to 3; n is 2 to 4 and x is 1 to 5; and the pharmaceutically acceptable salts thereof.

7. A pharmaceutical composition comprising a compound of structure (I), or a pharmaceutically acceptable salt thereof, as defined in claim 1 and a pharmaceutically acceptable carrier.

8. A method for treating inflammatory, painful or allergic conditions in a mammal which comprise the administration to said mammal of an effective amount of a compound selected from those of formula (I), or a pharmaceutically acceptable salt thereof, as claimed in claim 1.

* * * * *